United States Patent [19]

Lahners et al.

[11] Patent Number: 4,997,930
[45] Date of Patent: Mar. 5, 1991

[54] CLONING OF COMPLEMENTARY DNA ENCODING MAIZE NITRITE REDUCTASE

[75] Inventors: Kristine N. Lahners, Durham, N.C.; Steven J. Rothstein, Guelph, Canada

[73] Assignee: Ciba-Geigy Corporation, Ardsley, N.Y.

[21] Appl. No.: 324,154

[22] Filed: Mar. 16, 1989

[51] Int. Cl.$^5$ ............ C07H 21/04; C12P 21/02; C12N 15/00; C12N 1/00

[52] U.S. Cl. ............ 536/27; 435/69.1; 435/70.1; 435/172.3; 435/317.1; 435/240.4; 435/320.1; 935/18; 935/21; 935/35; 935/64; 935/78; 935/79

[58] Field of Search ............ 435/320, 317.1, 240.4, 435/69.1, 70.1; 536/27

[56] References Cited

PUBLICATIONS

Back et al. 1988 (Apr.) Mol Gen Genet 212:20-26.
Cheng et al. 1986, Proc. Natl. Acad. Sci. USA 83:6825-6828.
Lahners et al. 1988, Plant Physiol. 88:741-746.
Calza et al., Mol. Gen. Genet. 209:552-562 (1987).
Crawford et al., Proc. Natl. Acad. Sci. USA 83:8073-8076 (1986).

*Primary Examiner*—Charles F. Warren
*Assistant Examiner*—P. Rhodes
*Attorney, Agent, or Firm*—Henry P. Nowak; Steven R. Lazar

[57] ABSTRACT

Maize cDNA coding for nitrite reductase is cloned, using a spinach nitrite reductase cDNA as a heterologous probe, and is characterized. A method is provided to use the cloned maize nitrite reductase cDNA to determine the number of nitrite reductase genes per maize genome and to study nitrite reductase mRNA regulation in maize.

4 Claims, 5 Drawing Sheets

FIG. 1A

```
   1  gaattccggg ccgcacaggg cgcgcccgcg cggccgtctc cgtgccgccg
  51  ccggcggggg agcaggtccc gacggagcgg ctggagccga gggtcgagga
 101  gcgggcgggc gggtactggg tcctcaagga gaagtaccgg gcggggctga
 151  acccgcagga gaaggtgaag ctggagaagg agcccatggc gctgttcatg
 201  gagggcggca tccaggacct ggccagggtc cccatggagc agatcgacgc
 251  cgccaagctc accaaggacg acgtcgacgt ccgcctcaag tggctcggcc
 301  tcttccaccg ccgcaagcac cagtacgggc ggttcatgat gcggctgaag
 351  ctgcccaacg gcgtgacgac gagcgagcag acgcggtacc tggcgagcgt
 401  catcgaggcg tacggcgccg acgggtgcgc ggacgtgacc acccggcaga
 451  actggcagat ccgcggggtg acgctcccgg acgtcccggc catcctggac
 501  ggcctccgcg ccgtcggcct caccagcctg cagagcggca tggacaacgt
 551  gcgcaacccc gtcggcaacc cgctcgccgg cgtcgacccc cacgagatcg
 601  tcgacacgcg cccctacacc aaccttctct cctcctacgt caccaacaac
 651  tcccagggga accccacaat caccaacctg ccgaggaaat ggaacgtctg
 701  cgtcatcggc tcgcatgacc tgtacgagca cccgcacatc aacgacctcg
 751  cgtacatgcc ggccgtcaag gacggcgagt tcggcttcaa ccttctggtg
 801  ggcgggttca tcagccccaa gaggtgggcc gaggcgttgc cgctcgacgc
 851  ctgggtcgcc ggggacgacg tcgtccccgt gtgcaaggcc atcctcgagg
 901  cgtaccggga cctcggctcc aggggcaacc ggcagaagac gcgcatgatg
 951  tggctcatcg acgagctcgg gatggaggtg ttccggtcgg aggtggagaa
1001  gaggatgccg aacggggtgc tggagcgcgc cgcgccggag gacctcgtcg
1051  acaagcgctg ggagcggcgg gactacctcg gcgtgcaccc gcagaagcag
1101  gaaggcctgt cgtacgtggg cctccacgtg ccggtgggcc ggctgcaggc
```

FIG. 1B

```
1151  cgcggacatg ttcgagctgg cgcggctcgc cgacgagtac ggcaccggcg
1201  agctccggct cacggtggag cagaacatcg tgctccccaa cgtcagcaac
1251  gagaggctcg acgcgctgct ggcggagccg ctgctgcagg agcagcggct
1301  ctcgccgcgg ccgtcgatgc tgctcagggg gctggtggcg tgcacgggca
1351  accagttctg cgggcaggcc atcatcgaga ccaaggcgcg ggcgctgcag
1401  gtggcgcggg aggtggagaa gcgcgtggcc gtgccgcggc cggtccgcat
1451  gcactggacc ggatgcccca acagctgcgg ccaggtgcag gtggcggaca
1501  tcggcttcat gggctgcctc accaaggaca gcgacggcaa gatcgtcgag
1551  gccgcggaca tcttcgtggg cggccgcgtc ggcagcgact cgcacctggc
1601  cgacgtctac cggaagtccg tgccgtgcaa ggacctggtg cccatcgtgg
1651  ccgacctctt ggtggagcgg ttcggggccg tgccgaggga gagggaggag
1701  gatgaggagt aggaccttcg tcaagcgccg gctgggactg tcctgaccta
1751  ttttatgagg tcttgattgg atgtatatat atattcatct taatctatat
1801  ggatttctga agtttgatct aaaaaaaaaa aaaaaccgga attc
```

```
  3 ........................GRTGRARAAVSVPPPAGEQV  22
                              |  ||  |   |||  |
  1 MASLPVNKIIPSSTTLLSSSNNNRRRNNSSIRCQKAVSPAAETAAVSPSV  50

23 PTERLEPRVEERAGGYWVLKEKYRAGLNPQEKVKLEKEPMALFMEGGIQD  72
    ||||||||| |||||||| || |||| ||||||||||| |||||||| |
 51 DAARLEPRVEER.DGFWVLKEEFRSGINPAEKVKIEKDPMKLFIEDGISD  99

73 LARVPMEQIDAAKLTKDDVDVRLKWLGLFHRRKHQYGRFMMRLKLPNGVT 122
    || | ||||| |  |||||||||||||||||||| ||||||||||||||
100 LATLSMEEVDKSKHNKDDIDVRLKWLGLFHRRKHHYGRFMMRLKLPNGVT 149

123 TSEQTRYLASVIEAYGADGCADVTTRQNWQIRGVTLPDVPAILDGLRAVG 172
    ||||||||||| || |||||||||||||||||| ||||||   |  | ||
150 TSEQTRYLASVIKKYGKDGCADVTTRQNWQIRGVVLPDVPEIIKGLESVG 199

173 LTSLQSGMDNVRNPVGNPLAGVDPHEIVDTRPYTNLLSSYVTNNSQGNPT 222
    |||||||||||||||||||| |||||||||| |||| |  |||  | ||
200 LTSLQSGMDNVRNPVGNPLAGIDPHEIVDTRPFTNLISQFVTANSRGNLS 249

223 ITNLPRKWNVCVIGSHDLYEHPHINDLAYMPAVKDGEFGFNLLVGGFISP 272
    ||||||||| ||||||||||||||||||||||   ||||||||||||||
250 ITNLPRKWNPCVIGSHDLYEHPHINDLAYMPATKNGKFGFNLLVGGFFSI 299

273 KRWAEALPLDAWVAGDDVVPVCKAILEAYRDLGSRGNRQKTRMMWLIDEL 322
    ||   |||||||| |||||||||| ||| ||||| ||||| ||||||||
300 KRCEEAIPLDAWVSAEDVVPVCKAMLEAFRDLGFRGNRQKCRMMWLIDEL 349

323 GMEVFRSEVEKRMPNGVLERAAPEDLVDKRWERRDYLGVHPQKQEGLSYV 372
    ||| |||||||||| |||||   | ||| ||||| |||||||||||| |
350 GMEAFRGEVEKRMPEQVLERASSEELVQKDWERREYLGVHPQKQQGLSFV 399

373 GLHVPVGRLQAADMFELARLADEYGTGELRLTVEQNIVLPNVSNERLDAL 422
    || |||||||| | ||||| || ||||||||||||| | |||||  | |
400 GLHIPVGRLQADEMEELARIADVYGSGELRLTVEQNIIIPNVENSKIDSL 449

423 LAEPLLQEQRLSPRPSMLLRGLVACTGNQFCGQAIIETKARALQVAREVE 472
    | ||| |  | ||  |||||||||||||||||||||||||||| |  |
450 LNEPLLKE.RYSPEPPILMKGLVACTGSQFCGQAIIETKARALKVTEEVQ 498

473 KRVAVPRPVRMHWTGCPNSCGQVQVADIGFMGCLTKDSDGKIVEAADIFV 522
     | | |||||||||||||||||||||||||||| |||   |||||||||
499 RLVSVTRPVRMHWTGCPNSCGQVQVADIGFMGCMTRDENGKPCEGADVFV 548

523 GGRVGSDSHLADVYRKSVPCKDLVPIVADLLVERFGAVPREREEDEE    569
    |||||||||| || |||||||||||| |  ||||||||||||||||
549 GGRIGSDSHLGDIYKKAVPCKDLVPVVAEILINQFGAVPREREEEAE*   595
```

FIG. 2

Leaf Root

CLONING OF COMPLEMENTARY DNA ENCODING MAIZE NITRITE REDUCTASE

FIELD OF THE INVENTION

This invention relates to cloning of plant genes and in particular, to isolating and cloning DNA coding for maize nitrite reductase and to methods of using the DNA for studying the regulation of the nitrite reductase gene at the mRNA level in maize.

BACKGROUND OF THE INVENTION

Nitrite reductase (EC 1.6.6.4) is an enzyme that catalyzes the reduction of nitrite to ammonia, a six-electron transfer reaction in which ferredoxin is the physiological electron donor. This is an important reaction in plants and is part of the nitrate assimilatory pathway in which glutamine is the end product. Between one and three isozymes of nitrite reductase appear to be present in various plants, with two such isozymes having been detected in maize. The results in maize, however, are unclear, and a better method is needed to determine the number of isozymes in particular cultivars of maize.

A nitrite reductase gene from spinach, a dicotyledenous plant (dicot), has been cloned; however, nitrite reductase genes have not yet been cloned from monocotylenous plants (monocots). Spinach, soybeans, and cotton are representative examples of dicots, while monocots include plants such as wheat, corn and rice. Monocots, including cereal grains, are of great agronomic importance and make up a large percentage of the earth's food supply. In addition, to their differing external leaf appearance, monocots and dicots are very different in their biochemistry, and in their developmental and morphological organization. Because of the significant differences between dicots and monocots, laboratory and field researchers routinely must employ different techniques and materials to study the genetic characteristics and their growth characteristics of the two groups.

Unlike nitrite reductase, nitrate reductase cDNA clones have been isolated from a variety of plants and have enabled investigators to determine the enhancing effect of the addition of nitrate on nitrate reductase activity levels in those plants (Calza et al., Mol. Gen. Genet. 209:552-562, 1987; Cheng et al., Proc. Natl. Acad. Sci. USA 83:6825-6828, 1986; and Crawford et al., Proc. Natl. Acad. Sci. USA 83:8073-8076, 1986). These papers and all other publications cited herein are hereby incorporated herein by reference.

Isolation of maize nitrite reductase complementary DNA according to this invention makes it possible to determine the effect of various environmental conditions, including the presence of nitrate, on the level of nitrite reductase mRNA of maize plants grown under the selected conditions.

It is therefore an object of this invention to provide a method to clone nitrite reductase DNA of maize.

It is a further object of this invention to provide a cloned nitrite reductase DNA that may be used to study nitrite reductase gene regulation in maize under various plant growth conditions.

It is a further object of this invention to provide methods to use a cloned nitrite reductase DNA to study the nitrate assimilation process, including nitrite reductase gene regulation, in maize.

It is a further object of this invention to provide a method to determine the number of nitrite reductase genes in maize.

Other objects and advantages will be more fully apparent from the following disclosure and appended claims.

SUMMARY OF THE INVENTION

In the invention, maize cDNA coding for nitrite reductase is cloned, using the spinach nitrite reductase gene as a heterologous probe. In a further aspect of the invention, a method is provided to use the cloned maize nitrite reductase cDNA to determine the number of nitrite reductase genes per maize genome and to study nitrite reductase mRNA regulation and nitrate assimilation in maize.

Other aspects and features of the invention will be more fully apparent from the following disclosure and appended claims.

BRIEF DESCRIPTION OF THE DRAWINGS

FIGS. 1A and 1B together are a representation of the nucleotide sequence of the maize nitrite reductase clone pCIB808.

FIG. 2 is an amino acid sequence comparison between the spinach nitrite reductase and the maize nitrite reductase cloned in this invention.

FIG. 4 is an autoradiograph showing the results of nitrate induction in maize green tissue and roots according to the method of analysis of the invention.

DETAILED DESCRIPTION OF THE INVENTION AND PREFERRED EMBODIMENTS THEREOF

Figure 3:
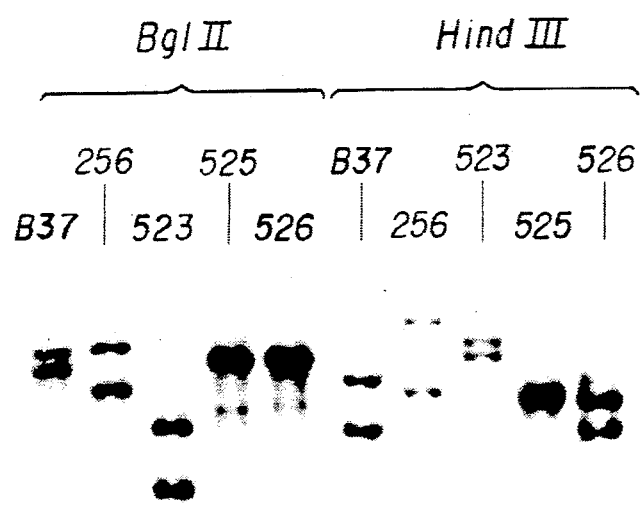
FIG. 3 is an autoradiograph showing the results of the genomic analysis of nitrite reductase genes in inbred maize lines according to the method of analysis of the invention, wherein the corn inbred lines were B37, T115, New York 821, Pa 32 and Tenn 232.

The present invention includes a method of cloning complementary DNA encoding maize nitrite reductase, the substantially pure maize nitrite reductase cDNA, phage containing the nitrite reductase cDNA, and methods of using the cDNA to study nitrite reductase mRNA and its regulation in maize.

In particular, the invention comprises: A method of cloning complementary DNA encoding maize nitrite reductase, comprising:
  (a) growing maize seedlings under conditions of nitrite reductase induction;
  (b) isolating poly A+ RNA from the leaves of the seedlings;
  (c) making double stranded cDNA from the RNA;
  (d) cloning the cDNA into a phage to form a phage cDNA clone;
  (e) hybridizing nick-translated nitrite reductase DNA from a non-maize plant to the phage cDNA clone;
  (f) using autoradiography to identify the maize nitrite reductase cDNA; and
  (g) amplifying the maize nitrite reductase cDNA.

Preferably, the phage that is used is λGT11 and the non-maize plant is spinach.

Furthermore, the invention comprises a method of evaluating the effect of various conditions on the levels of maize nitrite reductase mRNA, comprising:
  (a) obtaining cloned maize nitrite reductase cDNA;
  (b) growing seedlings under the conditions to be evaluated;

(c) isolating RNA from plant tissue of the maize seedlings; and (d) using the cDNA as a probe to analyze the amount of nitrite reductase mRNA in the plant tissue.

This method is useful in evaluating the effect of exposure of the maize plants to nitrate when the seedlings are grown hydroponically on a medium containing nitrate or nitrite.

The maize cDNA coding for nitrite reductase obtained in this invention may be employed to obtain a genomic clone containing the nitrate-inducible promoter of nitrite reductase using standard genetic probe and cloning techniques, wherein the cDNA made in the laboratory is used as a probe in a genomic library to find the inducible nitrite reductase promoter in the genomic DNA of the plant.

Preparation of a chimeric gene containing the putative promoter and a reporter gene, such as a beta-galactosidase gene or a beta-glucuronidase gene, and transformation of the chimeric gene into plants, allows confirmation that the reporter gene has become nitrate inducible by being linked with the promoter.

Using standard techniques (see Maniatis et al., chapter 9), this nitrate-inducible promoter may then be linked to other selected genes by constructing a plant-expressible chimeric gene comprising the inducible promoter and the coding sequence of the selected gene. The chimeric gene is transformed into a plant resulting in a plant in which nitrate stimulates the selected gene(s) in the plant.

Generally, this method for obtaining induction of a selected gene, comprises:

(a) obtaining cloned maize nitrite reductase cDNA according to the method of the invention;

(b) using the cDNA to obtain an inducible nitrite reductase promoter from genomic DNA;

(c) constructing a plant-expressible chimeric gene comprising the inducible promoter plus a coding sequence of interest; and (d) transforming the chimeric gene containing the inducible promoter into a plant.

Preferably, the promoter is inducible by nitrate to enable obtaining plants in which selected characteristics or reactions may be regulated by adjusting the nitrate level.

The features and advantages of the present invention will be more clearly understood by reference to the following examples, which are not to be construed as limiting the invention.

EXAMPLES

Example I:

Isolation of nitrite reductase DNA from maize

Maize plants (*Zea mays* L.) are grown in a vermiculite/sand mixture containing 20 mM nitrate to an age of about 8 days.

Poly A+ RNA is isolated from the leaves of the nitrate-induced plants and double stranded cDNA is made from the RNA using the method of Okayama et al., Mol. Cell. Biol. 2:161-170, 1982). EcoRI linkers (New England Biolabs, Beverly, Mass.) are added to the cDNA, and the cDNA is cloned into λGT11 (Young et al., Proc. Natl. Acad. Sci. USA 80:1194-1198, 1983). Nitrocellulose filter duplicates of the phage cDNA clones are hybridized with a nick-translated spinach nitrite reductase cDNA clone (Back et al., Mol. Gen. Genet. 212:20-26, 1988) in 50% formamide, 2× standard saline citrate (SSC), 0.2% SDS, and 5 mM EDTA at 42° C. (Maniatis et al., Molecular Cloning. A Laboratory Manual, Cold Spring Harbor Laboratory, Cold Spring Harbor, N.Y., 1982). The filters are washed in 2× standard saline citrate (SSC), 0.2% SDS, and 5 mM EDTA at 50° C.

Autoradiography using standard methods is done to identify phage plaques that hybridize to the spinach nitrite reductase. Phage from the plaques that hybridize to the spinach nitrite reductase cDNA clones are isolated. Fourteen hybridizing phage were isolated out of 270,000 plaques that were screened. Phage from the positive plaques are purified. The longest DNA inserts as determined after EcoRI digestion are subcloned into pUC19 (New England Biolabs, Beverly, Mass.); (Yanisch-Perron et al., Gene 33:103-119, 1985).

Example II:

RNA isolation and RNA blot analysis

Maize plants that are to be tested for induction of the nitrite reductase gene are harvested and then fast frozen in liquid $N_2$ and stored at $-80°$ C. Five grams of either the roots or leaves of the plants are placed in 10 ml of extraction buffer (50 mM Tris-HCl, pH 8.0, 4% sodium p-aminosalicylate, 1% sodium 1,5-naphthalenedisulfonate) and 10 ml of buffer-saturated phenol. After homogenization with a Brinkman Polytron (Kinematica, Luzern, Switzerland), the mixture is shaken for 20 minutes at 300 rpm. Ten ml of chloroform is added and the mixture is again shaken for ten more minutes before centrifugation at 7000 rpm in an SS34 Sorvall rotor. The aqueous phase is reextracted with 10 ml chloroform and LiCl added to a 2M concentration.

After overnight precipitation at 4° C., the RNA is sedimented in an SW41 rotor (Beckman Instruments, Inc., Fullerton, Calif.) at 25,000 rpm for 2 hours. The RNA is suspended in 1% SDS, 5 mM EDTA, 20 mM NaOAc, 40 mM Tris-HCl, pH 7.5, and is then precipitated with ethanol. The pellet precipitate is resuspended in $dH_2O$ and reprecipitated with ethanol. After a second resuspension in $dH_2O$, the concentration of the RNA is determined spectrophotometrically. Electrophoresis on a 1% agarose gel is used to determine the quality (absence of degradation) of the RNA, and ethidium bromide staining is used to examine the intactness of the ribosomal RNA.

Twenty ug of the total leaf RNA and 10 ug of the total root RNA are subjected to electrophoresis through a 1.2% agarose, 2.2M formaldehyde gel. The RNA is then blotted on to nitrocellulose filters (Maniatis et al.). An isolated fragment from pCIB801 (Example IV), is used for hybridization, under the same conditions (above) used for isolation of the cDNA clones. The filters are washed in 0.1× SSC, 0.1% SDS at 55° C.

Example III:

DNA isolation and DNA blot analysis

Maize DNA from inbred lines is obtained from S. Evola. Five micrograms of DNA are digested with restriction enzymes and subjected to electrophoresis in a 0.6% agarose gel. The hybridization conditions used are those of Klessig et al., Plant Mol. Biol. Rep. 1:12-18, 1983), with the filters being washed under the same conditions used for the RNA blot hybridizations.

Example IV:

Composition of maize nitrite reductase cDNA

The nitrite reductase cDNA is sequenced using the dideoxy chain termination method (Sanger et al., Proc. Natl. Acad. Sci. USA 74:5463-5467, 1977) using either single stranded M13 DNA or double stranded plasmid DNA as the template. The entire sequence of the nitrite reductase is confirmed by sequencing both strands of the DNA. One of the two longest inserts FIGS. 1A and 1B is found in pCIB808. Another cDNA clone (pCIB801) that was sequenced is identical to a corresponding region of pCIB808 (base pairs 276-1844 of pCIB808). The cDNA insert sequence of pCIB808 is 1844 base pairs long, which is about 150 bases shorter than the length of the mRNA. Using the nucleotide sequence of the maize nitrite reductase DNA, the protein amino acid sequence was deduced (FIGS. 1 and 2).

The cDNA clone (pCIB808) is 66% homologous at the nucleotide level to the spinach nitrite reductase gene. Unlike the spinach nitrite reductase gene, however, the maize DNA has a high G/C content (69.5%) as compared to that of the spinach gene (46%) and is 75% homologous at the amino acid level (FIG. 2). Further discussion of the protein sequence differences for the nitrite reductase of maize is found in Lahners et al., Plant Physiol. 88:741-746, 1988.

Example V:

Determination of the gene copy number of nitrite reductase in maize

DNA (5 ug) from highly nitrite reductase induced inbred lines of maize is digested with either of the restriction endonucleases, BglII or HindIII, neither of which cleaves within the nitrite reductase clone. After electrophoresis on a 0.6% agarose gel, the DNA is blotted on to nitrocellulose. DNA blot hybridization analysis of this DNA using the maize nitrite reductase cDNA clone (pCIB801) as the probe is shown in FIG. 3. In three of the five inbred lines tested to obtain the results shown in FIG. 3, there were two hybridizing fragments in both digests (BglII and HindIII), in a fourth inbred line there was a single BglII band and two HindIII bands, and in the fifth inbred line, there was a single band in each digest. DNA digested with EcoRI from all five inbred lines had two bands (not shown). Such evidence, along with other unpublished data, supports the theory that there are two nitrite reductase genes in maize.

Example VI:

Growing maize plants for induction studies

Maize seeds (*Zea mays* L.) are germinated in the dark for 3-4 days on germination paper soaked with distilled water. Seedlings with roots approximately 4 cm long are inserted into slits that have been cut into packing foam (Fidelity Products Co., Avon, Mass.). To grow the plants hydroponically, the foam pads bearing the seedlings are floated on the surface of the selected medium. A medium comprising 10 mM MES, pH 5.8 (McClure et al., Plant Physiol. 84:52-57, 1987) with no added nitrogen source is first used. When the plants are 10-12 cm tall (7-10 days after germination), they are induced with a nitrate source, selected from various nitrate salts, at a selected concentration (for example, 20 mM $Ca(NO_3)_2$, 10 mM MES, pH 5.8). The medium is circulated with a submersible pump (Little Giant Series One, Oklahoma City, Okla.). The plants are grown under a regime of 16 hr light and 8 hr dark or other selected plant growth conditions.

Example VII:

Studies of induction of maize nitrite reductase mRNA

Seedlings grown hydroponically, as in Example VI, for a 7-10 day period post germination in the absence of nitrate are then exposed to a nitrate-containing medium. After 90 minutes exposure to nitrate, the plants are harvested. Control plants are harvested just prior to the addition of nitrate to the medium.

Figure 4:
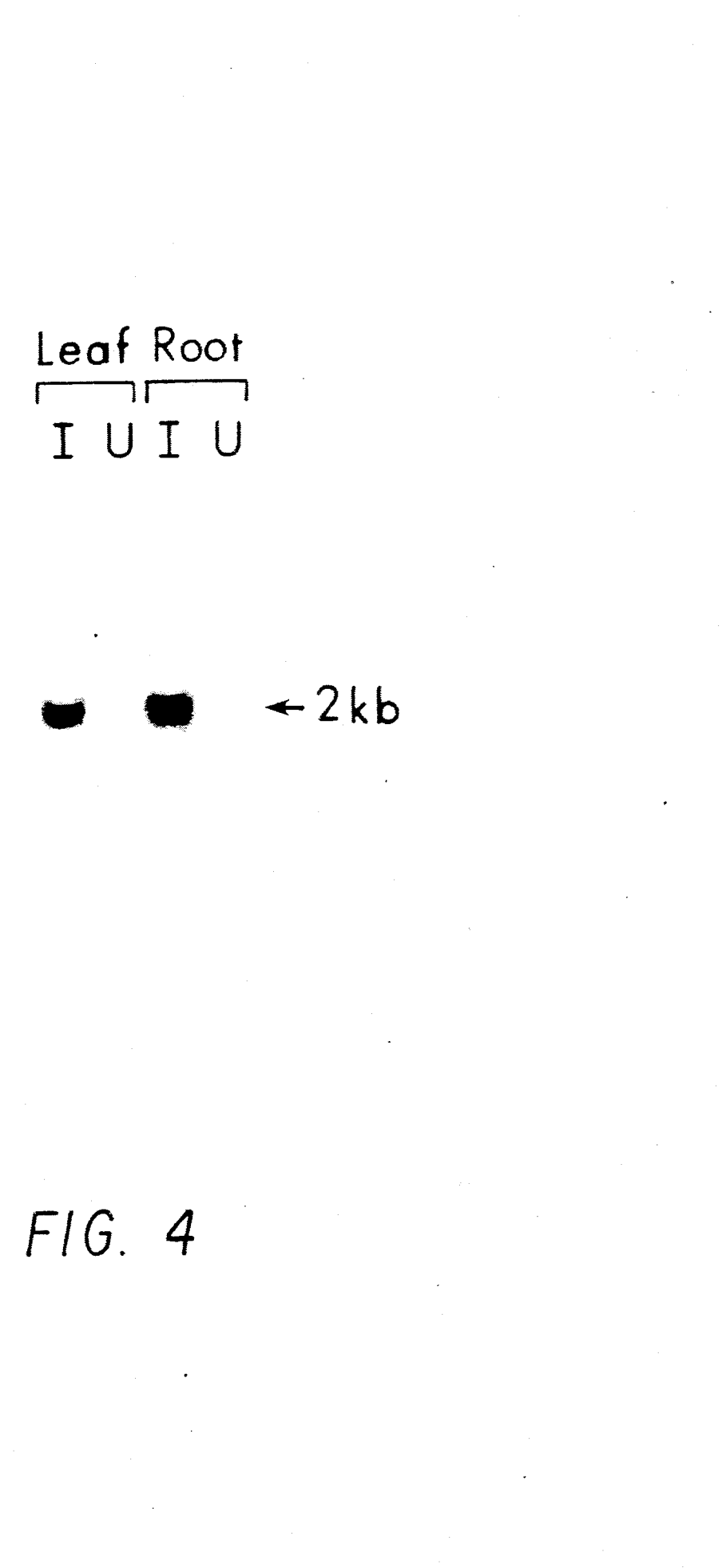

RNA is isolated from the leaves and roots of the nitrate-induced plants and the control plants Example II). A nick-translated cDNA clone is used as a probe under high stringency conditions (Maniatis et al.). Autoradiography is done according to standard techniques. The amount of nitrite reductase mRNA in the leaves and roots in induced plants as compared to uninduced plants is shown in FIG. 4. The roots generally have no detectable nitrite reductase prior to the addition of nitrate, while a small but reproducible amount of nitrite reductase is present in the control plant leaves. In both the roots and the leaves, substantial induction is observed as measured by an increase in the mRNA for nitrite reductase. Comparison with molecular weight standards (Bethesda Research Laboratories, Inc., Gaithersburg, Md.) indicates that the nitrite reductase mRNA is about 2 kb in length. In these experiments, control probe studies of the nitrocellulose with soybean actin cDNA verified that an equal amount of total mRNA was present in each lane (not shown).

Induction experiments similar to those described above but using nitrite rather than nitrate in the medium indicated that substantially lower levels of nitrite reductase were induced than with nitrate and that there were toxic effects on the leaves due to the nitrite.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A cloned DNA sequence consisting of a sequence encoding maize nitrite reductase.

2. An isolated DNA sequence according to claim 1, wherein the sequence comprises:

| 1 | gaattccggg | ccgcacaggg | cgcgcccgcg | cggccgtctc | cgtgccgccg |
|---|---|---|---|---|---|
| 51 | ccggcggggg | agcaggtccc | gacggagcgg | ctggagccga | gggtcgagga |
| 101 | gcgggcgggc | gggtactggg | tcctcaagga | gaagtaccgg | gcggggctga |
| 151 | acccgcagga | gaaggtgaag | ctggagaagg | agcccatggc | gctgttcatg |
| 201 | gagggcggca | tccaggacct | ggccagggtc | cccatggagc | agatcgacgc |
| 251 | cgccaagctc | accaaggacg | acgtcgacgt | ccgcctcaag | tggctcggcc |
| 301 | tcttccaccg | ccgcaagcac | cagtacgggc | ggttcatgat | gcggctgaag |
| 351 | ctgcccaacg | gcgtgacgac | gagcgagcag | acgcggtacc | tggcgagcgt |
| 401 | catcgaggcg | tacggcgccg | acgggtgcgc | ggacgtgacc | acccggcaga |

-continued

| | | | | |
|---|---|---|---|---|
| 451 actggcagat | ccgcggggtg | acgctcccgg | acgtcccggc | catcctggac |
| 501 ggcctccgcg | ccgtcggcct | caccagcctg | cagagcggca | tggacaacgt |
| 551 gcgcaacccc | gtcggcaacc | cgctcgccgg | cgtcgacccc | cacgagatcg |
| 601 tcgacacgcg | cccctacacc | aaccttctct | cctcctacgt | caccaacaac |
| 651 tcccagggga | accccacaat | caccaacctg | ccgaggaaat | ggaacgtctg |
| 701 cgtcatcggc | tcgcatgacc | tgtacgagca | cccgcacatc | aacgacctcg |
| 751 cgtacatgcc | ggccgtcaag | gacggcgagt | tcggcttcaa | ccttctggtg |
| 801 ggcgggttca | tcagccccaa | gaggtgggcc | gaggcgttgc | cgctcgacgc |
| 851 ctgggtcgcc | ggggacgacg | tcgtccccgt | gtgcaaggcc | atcctcgagg |
| 901 cgtaccggga | cctcggctcc | aggggcaacc | ggcagaagac | gcgcatgatg |
| 951 tggctcatcg | acgagctcgg | gatggaggtg | ttccggtcgg | aggtggagaa |
| 1001 gaggatgccg | aacggggtgc | tggagcgcgc | cgcgccggag | gacctcgtcg |
| 1051 acaagcgctg | ggagcggcgg | gactacctcg | gcgtgcaccc | gcagaagcag |
| 1101 gaaggcctgt | cgtacgtggg | cctccacgtg | ccggtgggcc | ggctgcaggc |
| 1151 cgcggacatg | ttcgagctgg | cgcggctcgc | cgacgagtac | ggcaccggcg |
| 1201 agctccggct | cacggtggag | cagaacatcg | tgctccccaa | cgtcagcaac |
| 1251 gagaggctcg | acgcgctgct | ggcggagccg | ctgctgcagg | agcagcggct |
| 1301 ctcgccgcgg | ccgtcgatgc | tgctcagggg | gctggtggcg | tgcacgggca |
| 1351 accagttctg | cgggcaggcc | atcatcgaga | ccaaggcgcg | ggcgctgcag |
| 1401 gtggcgcggg | aggtggagaa | gcgcgtggcc | gtgccgcggc | cggtccgcat |
| 1451 gcactggacc | ggatgcccca | acagctgcgg | ccaggtgcag | gtggcggaca |
| 1501 tcggcttcat | gggctgcctc | accaaggaca | gcgacggcaa | gatcgtcgag |
| 1551 gccgcggaca | tcttcgtggg | cggccgcgtc | ggcagcgact | cgcacctggc |
| 1601 cgacgtctac | cggaagtccg | tgccgtgcaa | ggacctggtg | cccatcgtgg |
| 1651 ccgacctctt | ggtggagcgg | ttcggggccg | tgccgaggga | gagggaggag |
| 1701 gatgaggagt | aggaccttcg | tcaagcgccg | gctgggactg | tcctgaccta |
| 1751 ttttatgagg | tcttgattgg | atgtatatat | atattcatct | taatctatat |
| 1801 ggatttctga | agtttgatct | aaaaaaaaaa | aaaaaccgga | attc |

3. Any complementary DNA clone containing the DNA strand consisting essentially of a portion of the maize nitrite reductase insert of pCIB808 according to claim 2 having at least 50 nucleotides, wherein said complementary DNA clone codes for a protein having nitrite reductase activity.

4. The complementary DNA strand in pCIB808, which DNA strand codes for the mRNA of maize nitrite reductase.

* * * * *